United States Patent [19]
Kojima et al.

[11] Patent Number: 6,007,688
[45] Date of Patent: Dec. 28, 1999

[54] WIDE RANGE AIR/FUEL RATIO SENSOR HAVING ONE ELECTROCHEMICAL CELL

[75] Inventors: Takao Kojima, Nagoya; Koichi Takahashi, Kani; Mitsunori Ooi, Kasugai; Takuya Saito, Kounan, all of Japan

[73] Assignee: NGK Spark Plug Co., Ltd., Aichi, Japan

[21] Appl. No.: 08/980,865

[22] Filed: Dec. 1, 1997

[30] Foreign Application Priority Data

Nov. 29, 1996 [JP] Japan ................................. 8-319809

[51] Int. Cl.⁶ .................................................. G01N 27/407
[52] U.S. Cl. ........................ 204/426; 204/402; 204/425; 204/427; 204/429
[58] Field of Search .................... 204/421–429, 204/402

[56] References Cited

U.S. PATENT DOCUMENTS

| | | | |
|---|---|---|---|
| 4,101,403 | 7/1978 | Kita et al. | 204/429 |
| 4,304,652 | 12/1981 | Chiba et al. | 204/426 |
| 4,305,803 | 12/1981 | Beyer et al. | 204/426 |
| 4,391,691 | 7/1983 | Linder et al. | 204/408 |
| 4,502,939 | 3/1985 | Holfelder et al. | 204/429 |
| 4,547,281 | 10/1985 | Wang et al. | 204/426 |
| 4,836,906 | 6/1989 | Yamada et al. | 204/425 |
| 5,302,276 | 4/1994 | Kato et al. | 204/426 |
| 5,389,225 | 2/1995 | Aagard et al. | 204/424 |
| 5,413,683 | 5/1995 | Murase et al. | 204/426 |
| 5,474,665 | 12/1995 | Friese et al. | 204/429 |
| 5,505,837 | 4/1996 | Friese et al. | 204/427 |

FOREIGN PATENT DOCUMENTS

| | | | |
|---|---|---|---|
| 63-52052 | 3/1988 | Japan | G01N 27/46 |
| 6-27080 | 2/1994 | Japan | G01N 27/419 |
| 8-166369 | 6/1996 | Japan | G01N 27/409 |
| 8/184577 | 7/1996 | Japan | G01N 27/419 |
| 8/220058 | 8/1996 | Japan | G01N 27/409 |
| 2195772 | 4/1988 | United Kingdom . | |

Primary Examiner—T. Tung
Attorney, Agent, or Firm—Sughrue, Mion, Zinn Macpeak & Seas, PLLC

[57] ABSTRACT

There are proposed an air/fuel ratio sensor which can detect a wide range of an air/fuel ratio and provides a simple structure, a superior mechanical strength or durability and a reduced manufacture cost, and a method of detecting the air/fuel ratio using the air/fuel ratio sensor. An air/fuel ratio sensor 1 is formed of a detecting portion 2 and a heater portion 3 laminated via a porous body 16. In the detecting portion 2, on an inner face of a plate-like solid electrolytic body 5, a reference electrode 7 is provided for controlling an oxygen gas diffusion rate, and on an outer face of the solid electrolytic body 5, a measurement electrode 6 is provided. A surface of the measurement electrode 6, on which the diffusion rate is not controlled, is covered with a protective layer 14 having an ventilation property to a degree to which the diffusion rate is not substantially controlled. A lead portion 7b of the reference electrode 7 is a porous layer which substantially controls the diffusion rate. The lead portion 7b is exposed to an exhaust gas via a connecting hole 13 which connects the lead potion 7b and the protective layer 14.

21 Claims, 10 Drawing Sheets

SENSOR OUTPUT (VOLTAGE)

FIG. 10

WIDE RANGE AIR/FUEL RATIO SENSOR HAVING ONE ELECTROCHEMICAL CELL

BACKGROUND OF THE INVENTION

1. Field of the Invention

The present invention generally relates to an air/fuel ratio sensor having one electrochemical cell, which can detect an air/fuel ratio in an exhaust gas exhausted from e.g. an automobile engine. More specifically this invention relates to an air/fuel ratio sensor using one oxygen-ion conductive cell, which can detect not only a stoichiometric air/fuel ratio ($\lambda=1$), but also an air/fuel ratio in a fuel-lean region ($\lambda>1$).

2. Description of the Prior Art

In recent years, most of automobile engines have been equipped with an air/fuel feedback control system to run the engines in a best condition reducing harmful exhaust gas components such as CO, NOx and HC. Either of two types of air/fuel ratio sensors is placed in the exhaust gas stream in such a feed back control system; one type is a stoichiometric air-fuel ratio sensor having one oxygen-ion conductive solid electrolyte cell and the other type is a universal or rather wide range air/fuel ratio sensor having two oxygen-ion conductive solid electrolyte cells.

The stoichiometric air/fuel sensor has one cell electrolyte cell that outputs an abrupt voltage variation-across two electrodes that sandwich the cell electrolyte, when the stoichiometric air/fuel mixture($\lambda=1$) is carbureted and combusted in an internal combustion engine. The stoichometric air/fuel sensor is often called a $\lambda$ sensor or a $\lambda$ air fuel sensor. This type sensor is described, e.g. in a U.S. Pat. No. 5,518,603.

On the other hand, the universal air/fuel sensor has two electrochemical cells, featuring in that the sensor can detect not only the stoichiometric air/fuel ratio($\lambda=1$) but also a universal or rather wide range air fuel ratio other than $\lambda=1$ (i.e. $\lambda>1$ and $\lambda<1$). The reason why such a wide range air fuel control can be done by this two-cell type sensor is that one of the cells is used as an oxygen pumping cell that pumps the oxygen out or into an oxygen reference chamber formed between the two cell of the sensor. If the pumping cell pumps out the oxygen from the reference chamber, it means that an air/fuel mixture in the engine is shifted to a fuel-lean region, i.e $\lambda>1$. If the pumping cell pumps oxygen into the reference chamber, it means that the air/fuel mixture shifted to a fuel-rich region (i.e. $\lambda<1$) is combusted in the engine.

A merit of using the universal sensor comprised of the two cell in such an air/fuel feedback control system is that an amount of fuel to be carbureted with the air into the engine can be linearly detected by a current flowing through the pumping cell across which a constant voltage is applied. This two-cell type sensor is disclosed, e.g. in a U.S. Pat. No. 5,194,135.

SUMMARY OF THE INVENTION

It is an object of the present invention to provide an inexpensive air/fuel sensor having one electrochemical cell, which detects two types of air/fuel ratios including a stoichiometric air/fuel ratio (i . e. $\lambda=1$) and also an air/fuel ratio that is higher than the stoichiometric air/fuel ratio (i.e. $\lambda>1$).

It is another object of the present invention to provide an air/fuel ratio sensor having a simple cell structure, by which sensor a stoichiometric air/fuel ratio and an air/fuel ratio in a fuel-lean region are accurately detected.

It is still another object of the present invention to provide a method of detecting a stoichiometric air/fuel ratio and an air/fuel ratio in a fuel-lean region, by using an air/fuel ratio sensor according to the invention.

Briefly, these and other objects of the present invention as hereinafter will become readily apparent as having been attained broadly by an air/fuel ratio sensor, including an electrochemical cell comprised of an oxygen-ion conductive solid electrolytic plate and two electrodes formed on the electrolytic plate.

This air/fuel sensor according to the invention, further includes two diffusion limit covers each covering the respective electrode; one of the electrodes is covered by a stronger or rather higher diffusion-limit cover than the other electrode, and the other electrode is covered by a weaker or rather lower diffusion-limit cover than the former one.

When the measurement gas enters through these diffusion-limit covers to contact the electrodes formed on the electrolytic plate, the electrode covered by the weaker-diffusion limit cover receives more gas molecules such as $O_2$ and $CO_2$ of the measurement gas than the other electrode covered by the stronger diffusion-limit cover. This is due to a difference in a gas-diffusion limit performance between the covers. This difference causes the electrochemical cell to produce a voltage across the electrodes formed on the oxygen conductive solid electrolytic plate, depending on a difference between oxygen concentrations of the gases each contacting the respective electrodes through the respective diffusion-limit cover.

In an aspect of the invention, a small current (due to oxygen ions) is flown across the sensor cell in the fuel-rich region($\lambda \leq 1$), by applying a constant voltage-across the electrodes in such manner that the electrode covered by the stronger diffusion-limit cover is electrically positive (i.e. in a positive polarity) and the electrode covered by the weaker diffusion-limit cover is electrically negative (i.e. in a negative polarity). The reason why such a constant voltage is applied across the electrodes in the fuel-rich region is to form an oxygen reference electrode (and/or an oxygen reference chamber) at the electrode covered by the stronger diffusion-limit cover. In other words, when the measurement gas in the fuel-rich region ($\lambda \leq 1$) approaches the two electrodes, there will appear an oxygen-concentration difference between the two electrodes, without causing a voltage reduction between the electrodes. However, when the measurement gas in a fuel-lean region (i.e. $\lambda \geq 1$: oxygen-containing gas) contacts the both electrodes, oxygen formed at the reference electrode moves to the other electrode, instantly reducing the voltage detected between the two electrodes to a minimum level. Therefor, this sensor outputs an abrupt voltage variation at around $\lambda=1$.

The detected abrupt voltage variation indicates the air/fuel ratio is stoichiometric; ($\lambda=1$).

In the other aspect of the invention, a constant voltage is applied across the electrodes in such a manner that the electrode covered by the stronger diffusion limit cover becomes electrically negative and the other electrode covered by the weaker diffusion limit cover becomes electrically positive, when the air fuel ratio in a fuel-lean region (i.e. $\lambda>1$) is to be determined. Under the voltage application in this way, the current that flows in the electrochemical cell becomes proportional to an oxygen concentration of the measurement exhaust gas in the fuel-lean region. Therefore the air fuel ratios in the fuel lean region is thus determined, based on the current that depends on the $O_2$ concentration of the measurement gas.

The air/fuel ratio sensor according to the invention attains a dual mode sensing mechanism by using only one cell; a stoichiometric $\lambda$ sensing and a lean-mode air/fuel sensing mechanism.

The wide air fuel ratio sensor according to the invention includes the stronger diffusion-limit cover having a gas diffusion limiting resistance of about $10^2$ to $10^4$ times higher, or preferably $1\times10^2$–$4\times10^3$ times higher than that of the weak diffusion-limit cover. A diffusion limit current flown from the electrode covered by the strong diffusion limit cover may be preferably designed to output an EMF on an order of 0.3 to 20 µA under a 5 percent oxygen concentrated gas at 750° C. These covers formed on the electrodes may be made of porous ceramic layer or ceramic plate, or of porous-metal layer including porous electrode metal.

The air/fuel ratio sensor according to the invention may further include the heater formed on then cell. In this instance, the position of the heater in the cell is important. The heater on the cell is preferably positioned closer to the weak diffusion limit cover formed on the electrode than to the strong diffusion limit cover formed on the other electrode (i.e. the reference electrode), because the λ air/fuel ratio control in the fuel-rich mode is instantly necessary just after the engine is started in a cold state with the fuel-rich mode ($\lambda \leq 1$). Further, the weak diffusion limit cover and a measurement electrode covered by the week diffusion limit cover are preferably positioned closest to an end of a cell rod in order to be exposed in the measurement gas thermodynamically faster than the strong diffusion limit cover and the reference electrode covered by the strong diffusion limit cover.

In a still other aspect of the air/fuel sensor according to the invention, the respective diffusion limit covers formed on the two electrodes may be designed as ventilating each other, either by the measurement gas or preferably by a flow channel formed between the diffusion limit covers. The difference in a gas diffusion limit performance between the electrodes can be adjusted by forming such a channel.

In a further aspect of the invention, the air/fuel sensor may further includes a voltage switch for switching a polarity of the voltage applied across the electrodes of the cell. This voltage switch may further comprise a voltage detector that detects an abrupt voltage variation around the stoichiometric air/fuel ratio region where λ is close to 1, a current detector that detects a current in a wide range of the fuel-rich air/fuel region where λ is larger than 1, and an electronic control unit that gives the voltage switch a timing for polarity change of the voltage applied across the electrodes.

BRIEF DESCRIPTION OF THE DRAWINGS

The invention will now be described by way of example, with reference to the accompanying drawings, in which.

DETAILED DESCRIPTION OF THE PREFERRED EMBODIMENTS

Embodiments of an air/fuel ratio sensor and a method of detecting an air/fuel ratio using the air/fuel ratio sensor are now described with reference to the accompanying drawings.

First Embodiment

An air/fuel ratio sensor of the first embodiment is attached to, for example, an exhaust system of an automobile for measuring an oxygen concentration or air/fuel ratio in a air/fuel mixture. By changing over measurement modes, an air/fuel ratio in the vicinity of λ=1 (theoretical or stoichiometric air/fuel ratio point) and an air/fuel ratio less than 14.4:1 in a lean region of λ>1 can be measured. In the air/fuel ratio sensor of the first embodiment, a rate of oxygen gas diffusion is controlled at a lead portion of a reference electrode.

Figure 1A:
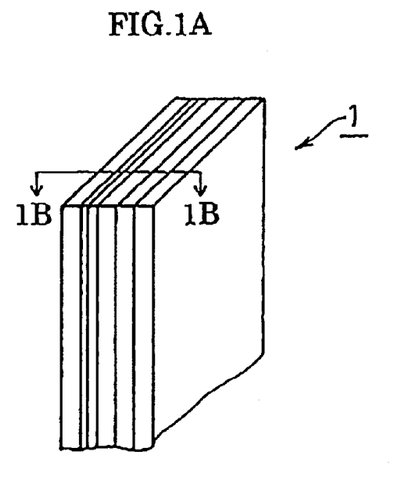
FIG. 1A is a partially broken perspective view of an air/fuel ratio sensor according to a first embodiment of the present invention.
Figure 1B:
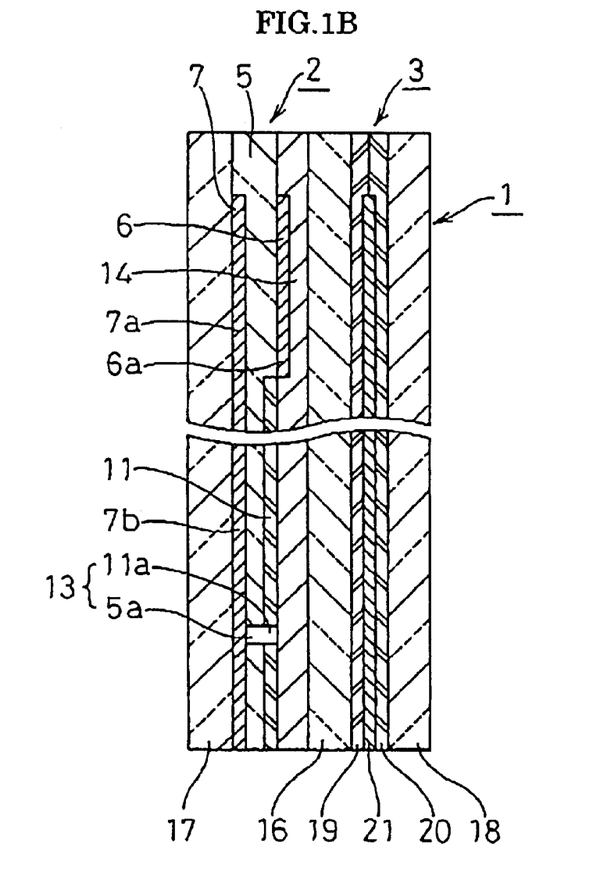
FIG. 1B is a cross-sectional view taken along line 1B–1B in FIG. 1A.
Figure 2:
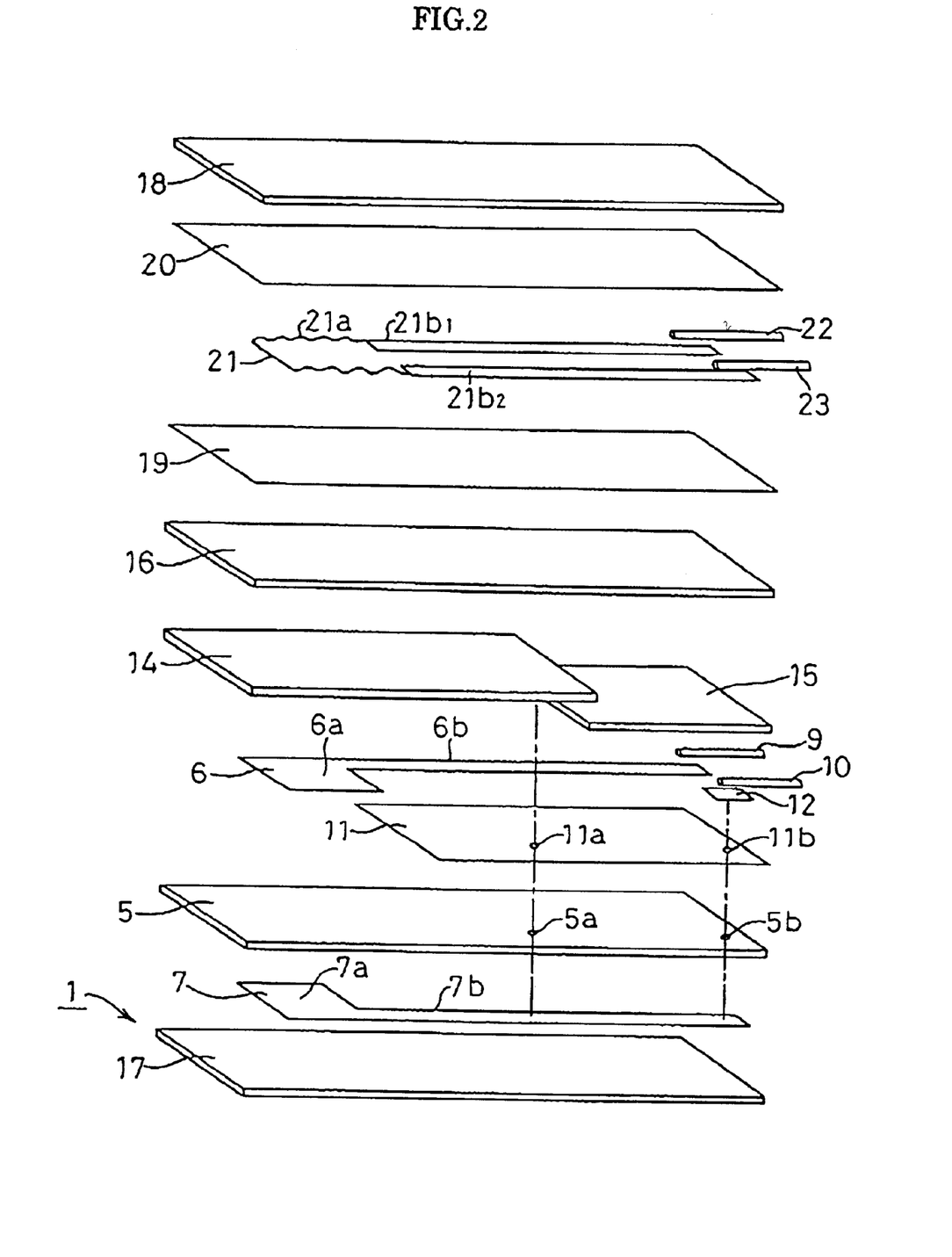
FIG. 2 is an exploded perspective view of the air/fuel ratio sensor according to the first embodiment.

As shown in FIGS. 1 and 2, an air/fuel ratio sensor 1 of the first embodiment is formed by a laminated plate with a thickness of 2.2 mm, a width of 3.5 mm and a length of 35 mm. The air/fuel ratio sensor 1 is generally constituted of a plate-like detecting portion 2 for detecting the air/fuel ratio and a plate-like heater portion 3 for heating the detecting portion 2. Details are as follows.

The detecting portion 2 is provided with a solid electrolytic body 5 formed of a 0.5 mm thick plate. On both sides of the solid electrolytic body 5, porous electrodes are formed. Of the porous electrodes, an inner one electrode 7 is a reference electrode on a side where a rate of oxygen gas diffusion is substantially controlled, and an outer one electrode 6 is a measurement electrode on a side where the rate of oxygen gas diffusion is not substantially controlled. The solid electrolytic body 5 is mainly constituted of $ZrO_2$ with 5 mol % of $Y_2O_3$ applied thereto, and can include 10 wt % or less of MgO, CaO, $SiO_2$ or other impurities. The electrodes 6 and 7 are mainly constituted of platinum and include about 20 wt. % of $ZrO_2$, $Al_2O_3$ and the like.

The electrodes 6 and 7 are constituted of electrode reaction portions 6a and 7a and lead portions 6b and 7b, respectively. The lead portions 6b and 7b are connected to lead wires 9 and 10 of platinum rhodium (with 13 wt. % rhodium included therein), respectively. The lead portion 7b of the reference electrode 7 is connected via through holes 5b and 11b formed in a rear end (lower end as seen in FIG. 1) of the solid electrolytic body 5 and a rear end of an insulation layer 11 of a connecting portion 12. The lead wire 10 is connected to the connecting portion 12. Also, to bring the lead portion 7b of the reference electrode 7 in contact with exhaust gas, middle portions of the solid electrolytic body 5 and the insulation layer 11 are provided with through holes 5a and 11a for forming a connecting hole 13.

Further, a porous protective layer 14 of $ZrO_2$ including 40 wt % of $Al_2O_3$ is provided to cover a front end of the measurement electrode 6 (from an upper part as seen in FIG. 1) to the vicinity of the through hole 5a. A rear end of the lead portion 6b and the lead wires 9 and 10 are covered with a protective layer 15 formed of $ZrO_2$. The protective layer 14 on the front end is a porous layer having a porosity such that the rate of oxygen gas diffusion is not substantially controlled, and the protective layer 15 on the rear end is a dense layer having no ventilation property.

So as to cover from a front end of the reference electrode 7 to the vicinity of a proximal end, a solid electrolytic body 17 having the same dimension and constitution as the solid electrolytic body 5 is provided, thereby protecting the reference electrode 7.

The lead portion 7b of the reference electrode 7 is connected via the connecting hole 13 to the front-end protective layer 14 which does not substantially control the diffusion rate, and, therefore, can contact exhaust gas via the connecting hole 13.

In the first embodiment, the rate of oxygen gas diffusion is substantially controlled by the lead portion 7b of the reference electrode 7. To suppress the ventilation property of the porous plate, i.e. enhance the air tightness, the particle diameter of platinum in the lead portion 7b is reduced.

As another method of substantially controlling the diffusion rate in the lead portion 7b, for example, at the time of laminating, the thickness of the lead portion 7b is greater than a thickness of the electrode reaction portion 7a. By controlling laminating pressure, the density of the lead portion 7b may be increased, thereby enhancing the air tightness. Alternatively, by applying glass or another aid only to the lead portion 7b, at the time of burning, the degree of sintering is increased, thereby enhancing the air tightness.

In the heater portion 3, on the solid electrolytic body 18 having the same dimension and composition as the solid electrolytic body 5, is provided a pair of insulation layers 19 and 20 each having a thickness of 30 $\mu$m and mainly constituted of $Al_2O_3$ which may include 5 wt % or less of MgO, CaO, $SiO_2$ and other impurities with the heating body 21 between the insulation layers 19 and 20. The heating body 21 is formed of a heat in portion 21a and a pair of heating lead portions $21b_1$, $21b_2$ connected to lead wires 22 and 23, respectively.

Further, the detecting portion 2 and the heater portion 3 are integrally bonded via a porous body 16 constituted of alumina or zirconia.

Current is applied to the heating body with a controller (not shown), so that a temperature in the vicinity of the electrode reaction portions 6a an 7a is kept at a predetermined value of 350° C. or more.

In the manufacture of the air/fuel ratio sensor 1 having the aforementioned structure, for example, green sheets of the solid electrolytic bodies 5, 17, 18, the insulation layers 11, 19, 20, the protective layers 14, 15, the porous layer 16 and the like are laminated. If necessary, conductive patterns are printed or formed otherwise on the respective green sheets, to form the electrodes 6, 8 and the heating body 21. A laminated body obtained in this manner is heated, for example, at 400° C. for ten hours to remove resin therefrom. Thereafter, the laminated body is fired at 1500° C. for two hours, thereby producing an integral bonded monolithic structure.

Figure 3A:
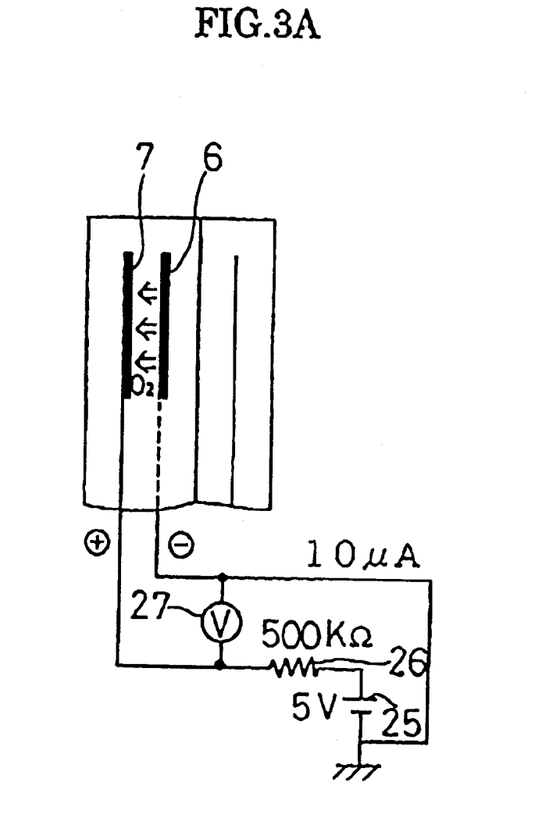
FIG. 3A is an explanatory view showing a device arrangement for detecting an air/fuel ratio using the air/fuel ratio sensor of the first embodiment.
Figure 3B:
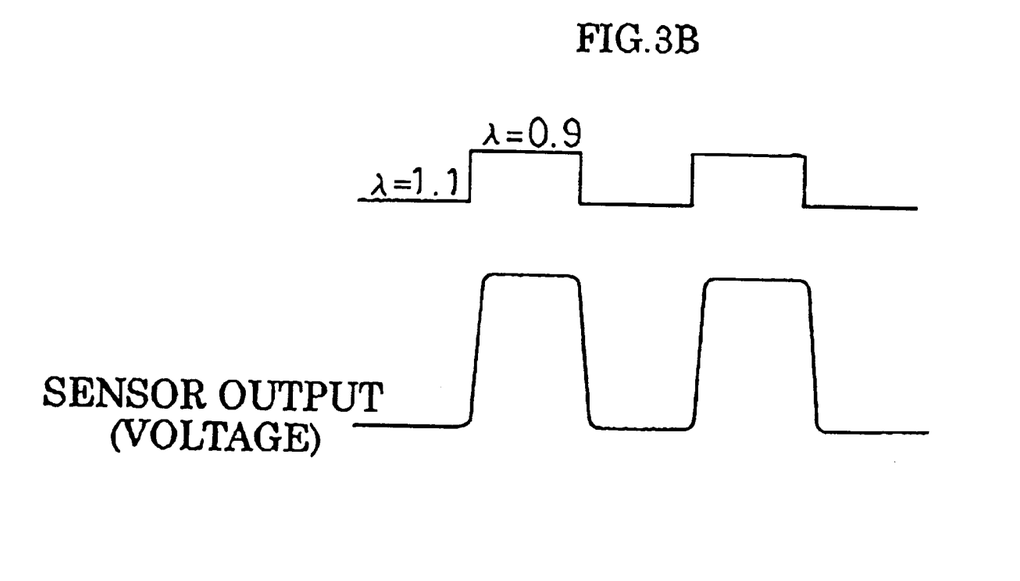
FIG. 3B is a graph showing a signal emitted from the air/fuel ratio sensor.
Figure 4A:
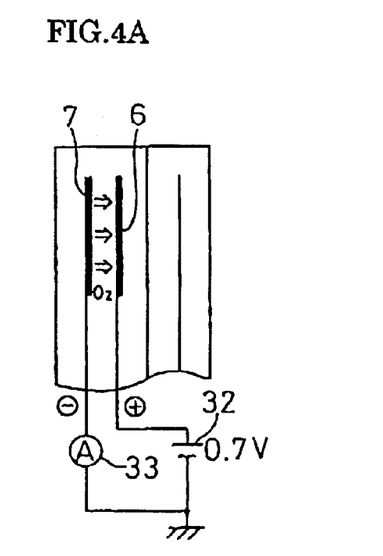
FIG. 4A is an explanatory view showing another device arrangement for detecting the air/fuel ratio using the air/fuel ratio sensor of the first embodiment.
Figure 4B:
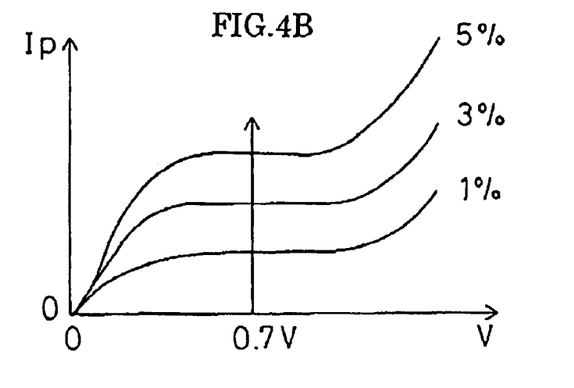
FIG. 4B is a graph showing a relationship between current and voltage of the signal emitted from the air/fuel ratio sensor.
Figure 4C:
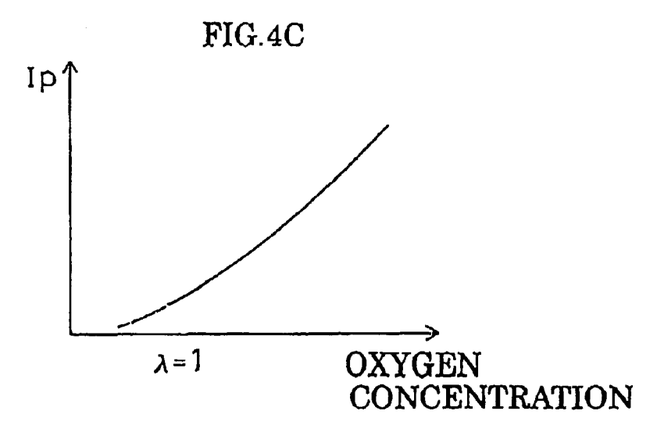
FIG. 4C is a graph showing a relationship between a current of the signal and an oxygen concentration.

A method of detecting an air/fuel ratio by using the air/fuel ratio sensor 1 obtained in this manner is now described referring to FIGS. 3 and 4.

When the air/fuel ratio sensor 1 of the first embodiment is used as a stoichiometric air/fuel ratio sensor, i.e. when the air/fuel ratio in the vicinity of $\lambda=1$ is detected, as shown in FIG. 3A, the reference electrode 7 is connected to a plus side (positive pole), and the measurement electrode 6 is connected to a minus side (negative pole). By applying a current of 10 $\mu$A between the electrodes 6 and 7 from an external power source 25 of 5V via a connection resistance 26 of 500 k$\Omega$, oxygen is pumped and supplied from the measurement electrode 6 toward the reference electrode 7.

An electromotive force generated in this manner between the electrodes 6 and 7 is measured with a voltmeter 27 connected to a position shown in FIG. 3A, and used as a sensor output of the air/fuel ratio sensor 1.

As shown in FIG. 3B, for example, when the air/fuel ratio of the exhaust gas changes from lean ($\lambda=1.1$) to rich ($\lambda=0.9$), the sensor output largely varies in accordance with the change in the air/fuel ratio. An actual condition of change in air/fuel ratio can be known from a condition of variation in sensor output. Therefore, by using the sensor output, the air/fuel ratio can be feedback-controlled to $\lambda=1$. For example, when the sensor output provides a value indicating that the air/fuel ratio is rich, the quantity of fuel is reduced. Conversely, when the sensor output provides a value inidicating that the air/fuel ratio is lean, the quantity of fuel is increased. In this manner, the air/fuel ratio can be controlled to be a target air/fuel ratio of $\lambda=1$ in the embodiment.

On the other hand, when the air/fuel ratio sensor 1 is used as a lean region air/fuel ratio sensor, i.e. when the air/fuel ratio of $\lambda>1$ is detected, as shown in FIG. 4A, in reverse to the stoichiometric air/fuel ratio sensor shown in FIG. 3A, the reference electrode 7 is connected to a negative pole, and the measurement electrode 6 is connected to a positive pole. A voltage Vp of, for example, 0.7V is applied between the electrodes 6 and 7 from an external power source 32, and a current Ip flowing between the electrodes 6 and 7 is measured, for example, with an ammeter 33 connected to a position shown in FIG. 4A.

As shown in FIG. 4B, for example, when the oxygen concentration of the exhaust gas changes to 1%, 3% or 5%, the sensor output varies in the manner shown in this figure. Specifically, in the same manner as the sensor output in the limiting current system, when the specified voltage is applied, the current Ip increases as the oxygen concentration increases. Therefore, as shown in FIG. 4C, the oxygen concentration or air/fuel ratio can be detected based on the magnitude of the current Ip.

As aforementioned, when the air/fuel ratio sensor 1 of the first embodiment is operated as a stoichiometric air/fuel ratio sensor or a lean region air/fuel ratio sensor, the polarity of the electrodes 6 and 7 is reversed, thereby reversing the oxygen supply direction. Specifically, only by reversing the electrically conducting direction in the same air/fuel ratio sensor 1, different functions can be advantageously achieved. By using the air/fuel ratio sensor 1 of the first embodiment, a wide range of air/fuel ratio can be detected, and the air/fuel ratio in the vicinity of λ=1 can be measured precisely. Further, the structure of the stoichiometric air/fuel ratio sensor of the first embodiment is relatively simple and is superior in mechanical strength and cost to prior art designs.

Also when the air/fuel ratio sensor 1 of the first embodiment operates as the stoichiometric air/fuel ratio sensor, the atmosphere of the front-end protective layer 14 on which the diffusion rate is not controlled changes rapidly. Therefore, a high responsiveness can be obtained.

Further, when the air/fuel ratio sensor 1 operates as the lean region air/fuel ratio sensor, the electrodes 6 and 7 are exposed to the exhaust gas. Therefore, even when the actual air/fuel ratio becomes rich at the time of acceleration of the engine, no electromotive force is produced between the electrodes 6 and 7 and a precise sensor output can be obtained. Also, even when the air/fuel ratio momentarily becomes rich, in a diffusion limiting system, the oxygen quantity of the reference electrode 7 is in the vicinity of zero. Therefore, even when the measurement electrode 7 is exposed to a rich gas, only very small electromotive force is produced and, again, the air/fuel ratio can be detected precisely.

Second Embodiment

A second embodiment will now be described.

An air/fuel ratio sensor of the second embodiment is different in structure from the air/fuel ratio sensor 1 of the first embodiment. However, operation is almost the same. Therefore, different aspects only are primarily described.

Figure 5A:
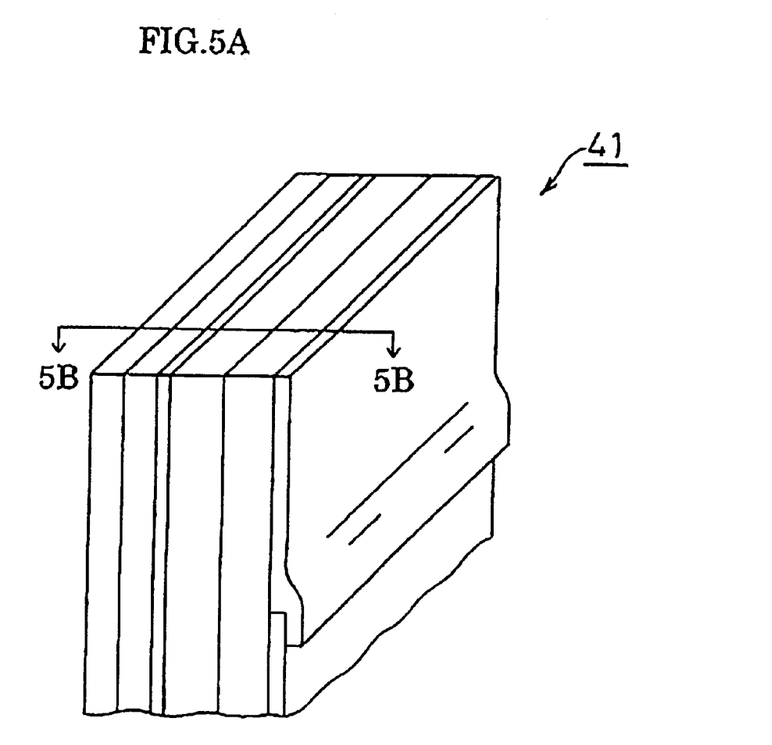
FIG. 5A is a partially broken perspective view of an air/fuel ratio sensor according to a second embodiment.
Figure 5B:
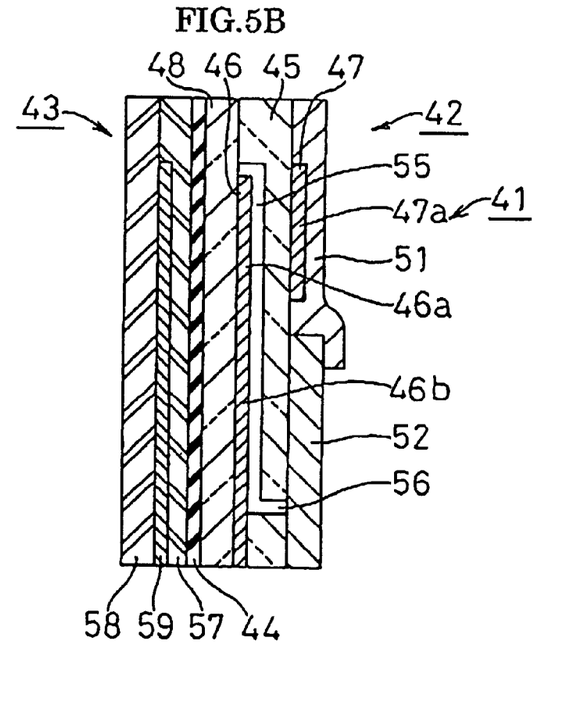
FIG. 5B is a cross-sectional view taken along line 5B–5B in FIG. 5A.

As shown in FIGS. 5A and 5B, an air/fuel ratio sensor 41 of the second embodiment is formed of a detecting portion 42 and a heater portion 43 bonded via a bonding layer 44. Especially on a protective layer on a reference electrode, the diffusion rate is controlled.

In the detecting portion 42, in the same manner as the first embodiment, a porous measurement electrode 47 formed of platinum or the like is provided on a measurement gas side of a plate-like solid electrolytic body 45 constituted of $ZrO_2$ or the like. A reference electrode 46 is provided on a plate-like solid electrolytic body 48 constituted of $ZrO_2$ or the like. The measurement electrode 47 is provided with a porous protective layer 51 covering an electrode reaction portion 47a. A rear end behind the electrode reaction portion 47a is covered with a porous protective layer 52.

Especially in the second embodiment, the protective layer 51 on the front end (the upper part as seen in FIG. 5B) is a porous layer having a ventilation property to a degree that the diffusion rate is not substantially controlled, and the protective layer 52 on the rear end is a porous layer has a ventilation property sufficiently low that the diffusion rate can be substantially controlled.

Also, a clearance 55 is provided along a surface of the reference electrode 46 on the side of the solid electrolytic body 45. A connecting hole 56 is provided for connecting the clearance 55 and the protective layer 52, i.e. connecting the reference electrode 46 via the clearance 55 to the exhaust gas.

In the heater portion 43, a pair of plate-like insulation layers 57, 58 constituted of $ZrO_2$, MgO, $Al_2O_3$ or another ceramics are provided. Between the insulation layers 57 and 58 is provided a heating body 59 constituted of platinum and the like.

In the manufacture of the air/fuel ratio sensor 41 with the aforementioned constitution, a laminated body (not shown) formed of laminated green sheets or the like is fired to form the detecting portion 42. In the same manner, a laminated body (not shown) formed of laminated green sheets or the like is fired to form the heater portion 43. The detection portion 42 and the heater portion 43 are bonded with a heat resistant adhesive constituted of, for example, cement or another inorganic material.

When the air/fuel ratio sensor 41 is operated as the stoichiometric air/fuel ratio sensor in the same manner as the first embodiment, oxygen is pumped from the measurement electrode 47 to the reference electrode 46. By using an electromotive force produced between the electrodes 47 and 48, the air/fuel ratio is detected. However, when the air/fuel ratio sensor 41 is operated as the lean-region air/fuel ratio sensor, oxygen is pumped from the reference electrode 46 to the measurement electrode 47. By using a current flowing between the electrodes 46 and 47, the air/fuel ratio is detected.

The second embodiment provides the same effect as the first embodiment. Additionally, since the clearance 55 on the reference electrode 46 is connected via the connecting hole 56 to the protective layer 52, and the oxygen gas diffusion is controlled in the protective layer 52, a degree of diffusion control can be adjusted minutely in the manufactured air/fuel ratio sensor 41.

When forming the reference electrode 46 of the second embodiment, the electrode reaction portion 46a need not differ in structure or air tightness from the lead portion 46b. Therefore, the reference electrode 46 can be easily formed.

Further, the detecting portion 42 and the heater portion 43 are separately fired and later bonded together. Therefore, even when either the detecting portion 42 or the heater portion 43 becomes defective, only operative portions can be combined for use and yield is enhanced thus reducing manufacture cost.

Third Embodiment

A third embodiment will now be described.

An air/fuel ratio sensor of the third embodiment is different in structure from the air/fuel ratio sensors of the first and second embodiments, however, operation is almost the same. Therefore, different aspects only are primarily described.

Figure 6A:
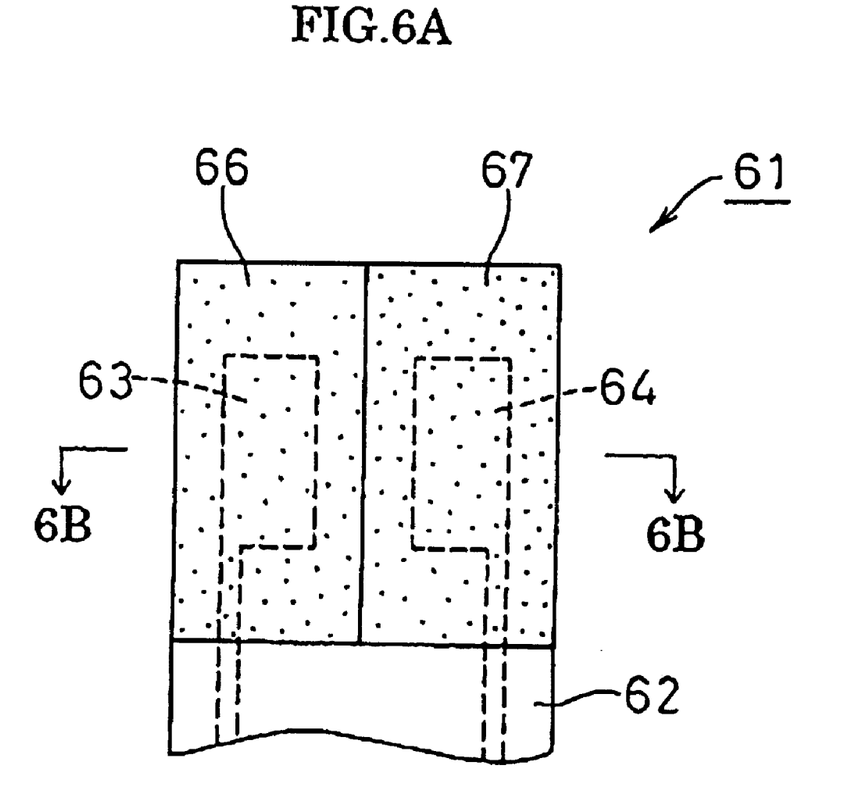
FIG. 6A is a partially broken plan view of an air/fuel ratio sensor according to a third embodiment.
Figure 6B:
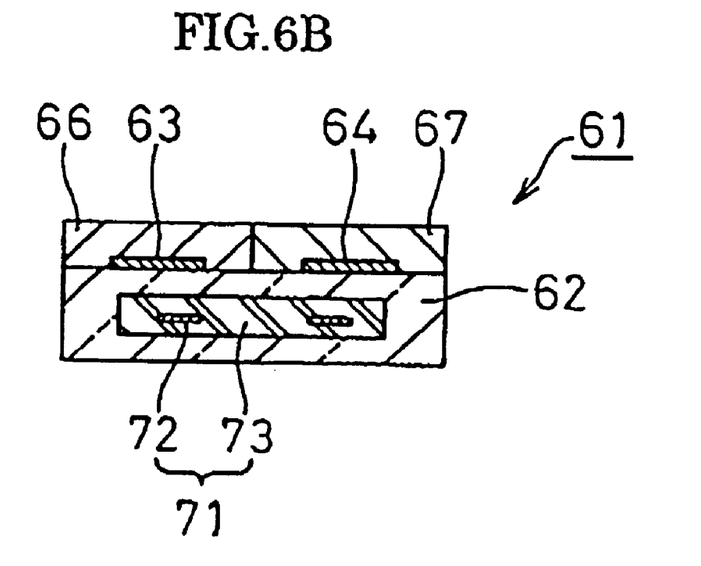
FIG. 6B is a cross-sectional view taken along line 6A–6A in FIG. 6A.

As shown in FIGS. 6A and 6B, in an air/fuel ratio sensor 61 of the third embodiment, on one face of a plate-like solid electrolytic body 62 formed, for example, of $ZrO_2$ or the like, a porous measurement electrode 63 and a reference electrode 64, both formed of platinum or the like, are disposed.

A surface of the measurement electrode 63 is covered with a porous protective layer 66 which has a ventilation property to a degree that the diffusion rate is not substantially controlled, and a surface of the reference electrode 64 is covered with a porous protective layer 67 which has a ventilation property sufficiently low that the diffusion rate can be substantially controlled. Although the protective layers 66 and 67 are both porous layers constituted of, for example, $Al_2O_3$, they differ from each other in porosity, therefore ventilation property or air tightness.

A heater portion 71 provided in the solid electrolytic body 62 is constituted of an insulation layer 73 of $Al_2O_3$ or the like for covering a periphery of a heating body 72 of platinum or the like.

The air/fuel ratio sensor 61 of the third embodiment provides the same effect as the first embodiment.

Additionally, since the electrodes 63 and 64 are disposed only on one face of the plate-like solid electrolytic body 62, the air/fuel ratio sensor 61 can be easily manufactured.

Fourth Embodiment

A fourth embodiment will now be described.

An air/fuel ratio sensor of the fourth embodiment is different in structure from the air/fuel ratio sensors of the first to third embodiments, however, operation is almost the same. Therefore, different aspects only are primarily described.

Figure 7:
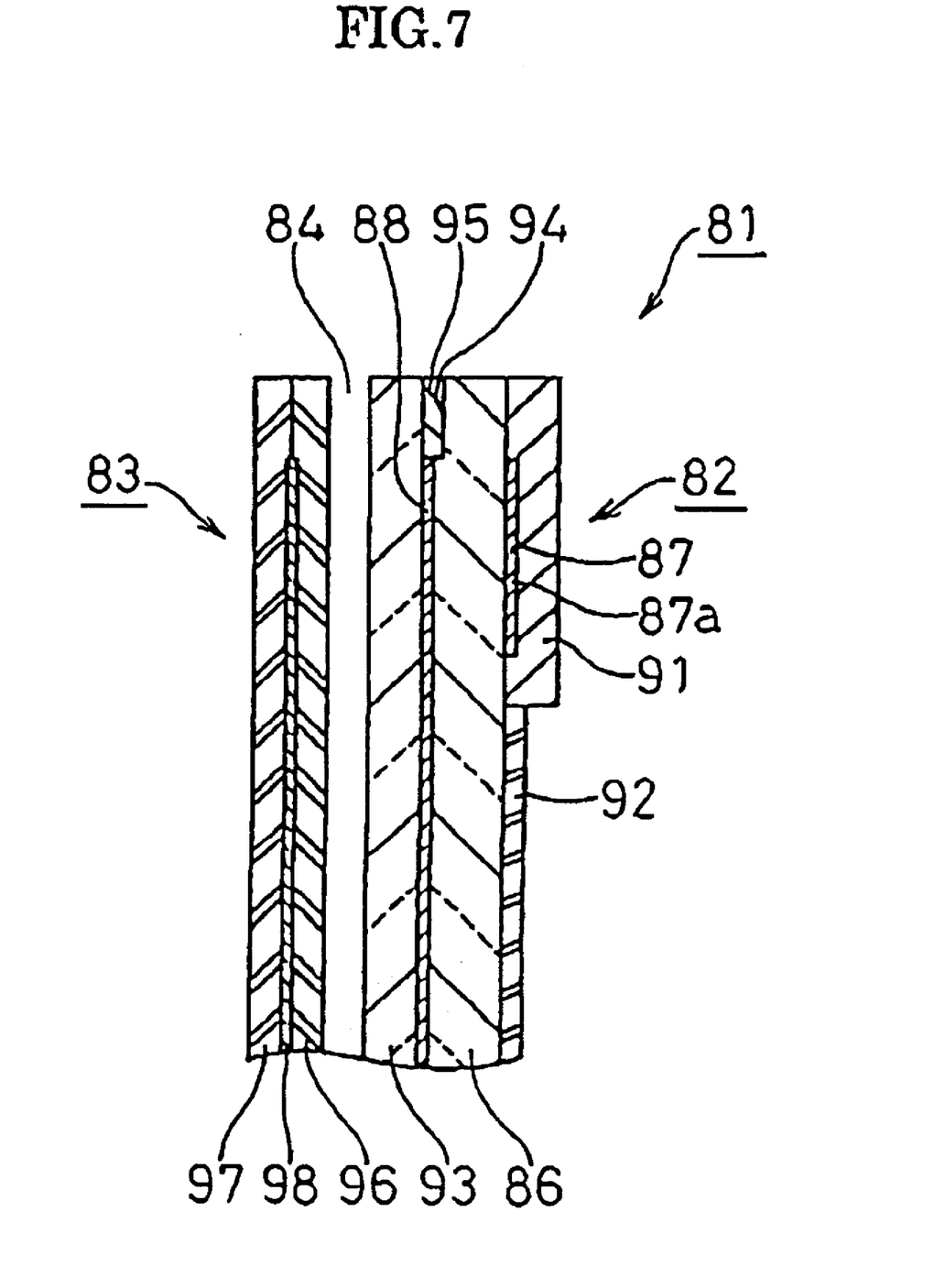
FIG. 7 is a partial cross-sectional view of an air/fuel ratio sensor according to a fourth embodiment.

As shown in FIG. 7, in an air/fuel ratio sensor 81 of the fourth embodiment, a detecting portion 82 and a beater portion 83 are disposed close to each other with a clearance 84 therebetween provided by a spacer (not shown).

In the detecting portion 82, on one face of a plate-like solid electrolytic body 86 formed, for example, of $ZrO_2$ or the like, a porous measurement electrode 87 formed of platinum or the like is disposed, and on the other face of the solid electrolytic body 86, a reference electrode 88 also formed of platinum or the like is disposed.

A surface of an electrode reaction portion 87a of the measurement electrode 87 is covered with a porous protective layer 91 formed, for example, of $Al_2O_3$ which has a ventilation property such that the diffusion rate is not substantially controlled, and a lead portion (not shown) of the measurement electrode 87 is covered with a protective layer 92 having no ventilation property and formed of, for example, $Al_2O_3$. Also, a surface of the reference electrode 88 on the side of the clearance 84 is covered with a plate-like solid electrolytic body 93 formed, for example, of $ZrO_2$.

In the fourth embodiment, a connecting hole 94 is formed in an upper end (an upper part as seen in the figure) of the reference electrode 88, to connect to the exhaust gas. A diffusion controlled layer 95 provided inside the connecting hole 94 has a ventilation property sufficiently low that the diffusion rate is substantially controlled.

Also, between plate-like insulation layers 96 and 97 both formed of $Al_2O_3$ or the like provided is a heating body 98 formed of platinum or the like.

The air/fuel ratio sensor 81 of the fourth embodiment provides the same effect as the first embodiment. Additionally, since the detecting portion 82 and the heater portion 83 are disposed with the clearance 84 therebetween, a current applied to the heating body 98 does not influence sensor output, and the air/fuel ratio can be effectively detected precisely. Further, since the air/fuel ratio sensor 81 is manufactured by using separate members, yield is advantageously enhanced. Further, even when materials different in thermal expansion are used, no warp or cracks arise.

Fifth Embodiment

A fifth embodiment will now be described.

An air/fuel ratio sensor of the fifth embodiment is different in structure from the air/fuel ratio sensors of the first to fourth embodiments, however, operation is almost the same. Therefore, different aspects only are primarily described.

Figure 8A:
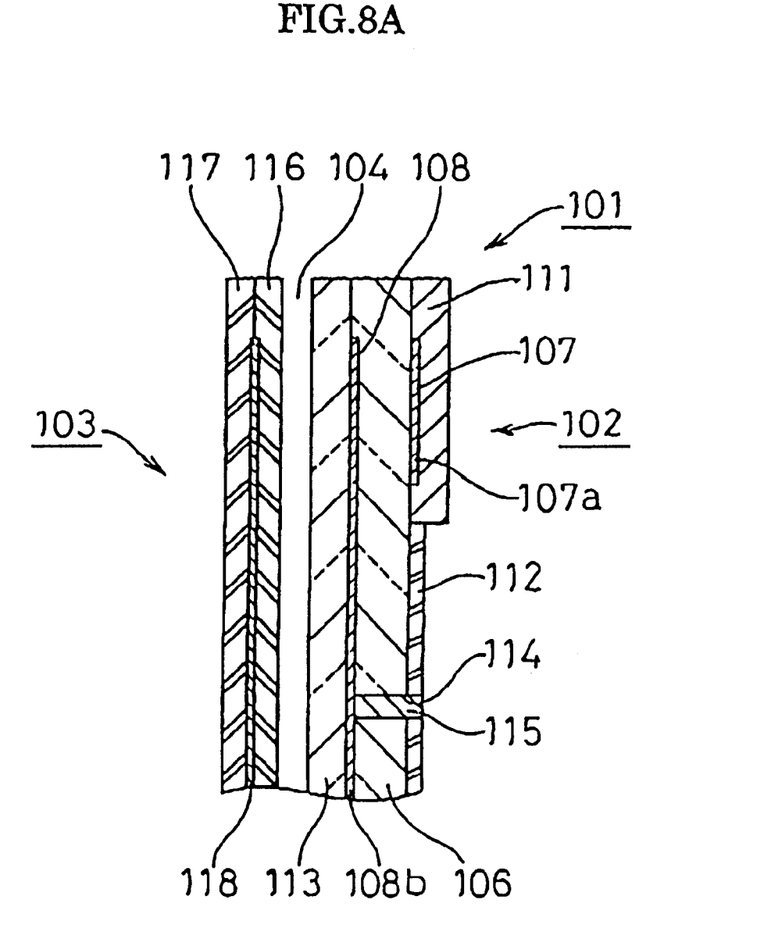
FIG. 8A is a partial cross-sectional view of an air/fuel ratio sensor according to a fifth embodiment.

As shown in FIG. 8A, in an air/fuel ratio sensor 101 of the fifth embodiment, a detecting portion 102 and a heater portion 103 are disposed close to each other with a clearance 104 made therebetween by a spacer (not shown).

In the detecting portion 102, on one face of a plate-like solid electrolytic body 106 formed, for example, of $ZrO_2$ or the like, a porous measurement electrode 107 formed of platinum or the like is disposed, and on the other face of the solid electrolytic body 106, a reference electrode 108 also formed of platinum or the like is disposed.

A surface of an electrode reaction portion 107a of the measurement electrode 107 is covered with a porous protective layer 111 formed, for example, of $Al_2O_3$ which has a ventilation property sufficient that the diffusion rate is not substantially controlled, and a lead portion (not shown) of the measurement electrode 107 is covered with an insulation layer 112 having no ventilation property and formed of, for example, $Al_2O_3$. Also, a surface of the reference electrode 108 on the side of the clearance 104 is covered with a solid electrolytic body 113 formed, for example, of $ZrO_2$.

Figure 8B:
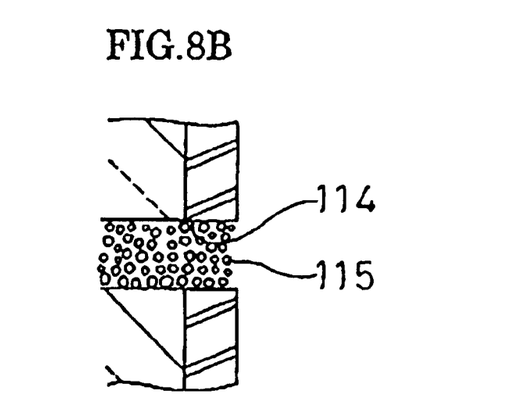
FIG. 8B is an enlarged view of a main portion of the air/fuel ratio sensor according to the fifth embodiment.

In the fifth embodiment, a connecting hole 114 connects a lead portion 108b of the reference electrode 108 to the exhaust gas. A porous diffusion controlled layer 115, provided inside the connecting hole 114 as shown in FIG. 8B, has a ventilation property sufficiently low that the diffusion rate is substantially controlled and is formed of, for example, $Al_2O_3$.

Also, in the heater portion 103, between plate-like insulation layers 116 and 117 both formed of $Al_2O_3$ or the like is provided is a heating body 118 formed of platinum or the like.

The air/fuel ratio sensor 101 of the fifth embodiment provides the same effect as the fourth embodiment.

This invention is not restricted to the aforementioned preferred embodiments. Modifications and alterations within the spirit and scope of the appended claims are also included.

Figure 9:
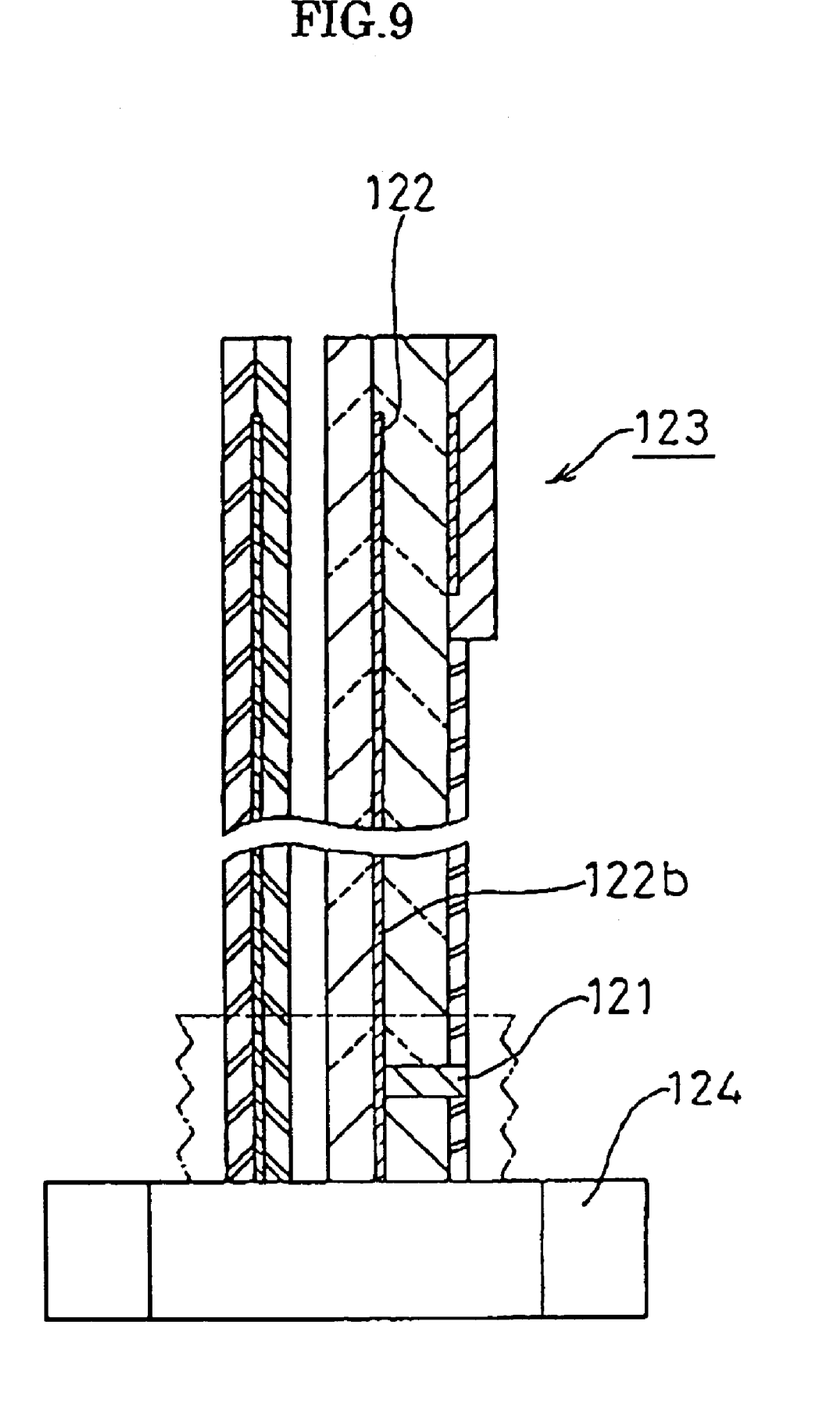
FIG. 9 is an explanatory view showing another air/fuel ratio sensor according to the invention.

For example, in the fifth embodiment, the connecting hole 114 for substantially controlling the diffusion rate is provided substantially in the middle of the lead portion 108b of the reference electrode 108. Alternatively, as shown in FIG. 9, a connecting hole 121 may be provided in a rear end (lower end as seen in the figure) of a lead portion 122b of a reference electrode 122 and in the vicinity of a cylindrical metal fitting 124 for attaching an air/fuel ratio sensor 123 to an exhaust pipe (not shown).

Since the connecting hole 121 is provided in the aforementioned position, the air/fuel ratio sensor 123 is less influenced by temperatures, as compared with the fifth embodiment. Even when the temperature of exhaust gas changes, the degree of diffusion rate control hardly varies. Therefore, the air/fuel ratio can be precisely detected.

As aforementioned, in the air/fuel ratio sensor according to the invention, both electrodes are exposed via the ventilating portions to the measurement gas, and both the ventilating portions have different ventilation properties. One of the ventilating portions has a function of substantially controlling the oxygen diffusion rate. By using the air/fuel ratio sensor, a wide range of air/fuel ratio can be detected. The air/fuel ratio sensor advantageously provides a simple structure, superior mechanical strength and durability, and a low manufacture cost.

In the method of detecting the air/fuel ratio according to the invention, the aforementioned air/fuel ratio sensor is used. By setting an oxygen pumping direction and measuring a produced electromotive force, the air/fuel ratio in the vicinity of $\lambda=1$ can be detected by the air/fuel ratio sensor as the stoichiometric air/fuel ratio sensor.

In the method of detecting the air/fuel ratio according to the invention, by applying voltage between the electrodes and measuring a flowing current value, the air/fuel ratio in the region of $\lambda>1$ can be detected by the aforementioned air/fuel ratio sensor as the lean region air/fuel ratio sensor.

In the method of detecting the air/fuel ratio according to the invention, by changing the condition of current or voltage applied to the air/fuel ratio sensor in accordance with the air/fuel ratio to be detected, the air/fuel ratio sensor can be used as the stoichiometric air/fuel ratio sensor or the lean region air/fuel ratio sensor. Therefore, with a simple constitution, a wide region of air/fuel ratio can be detected.

Figure 10:
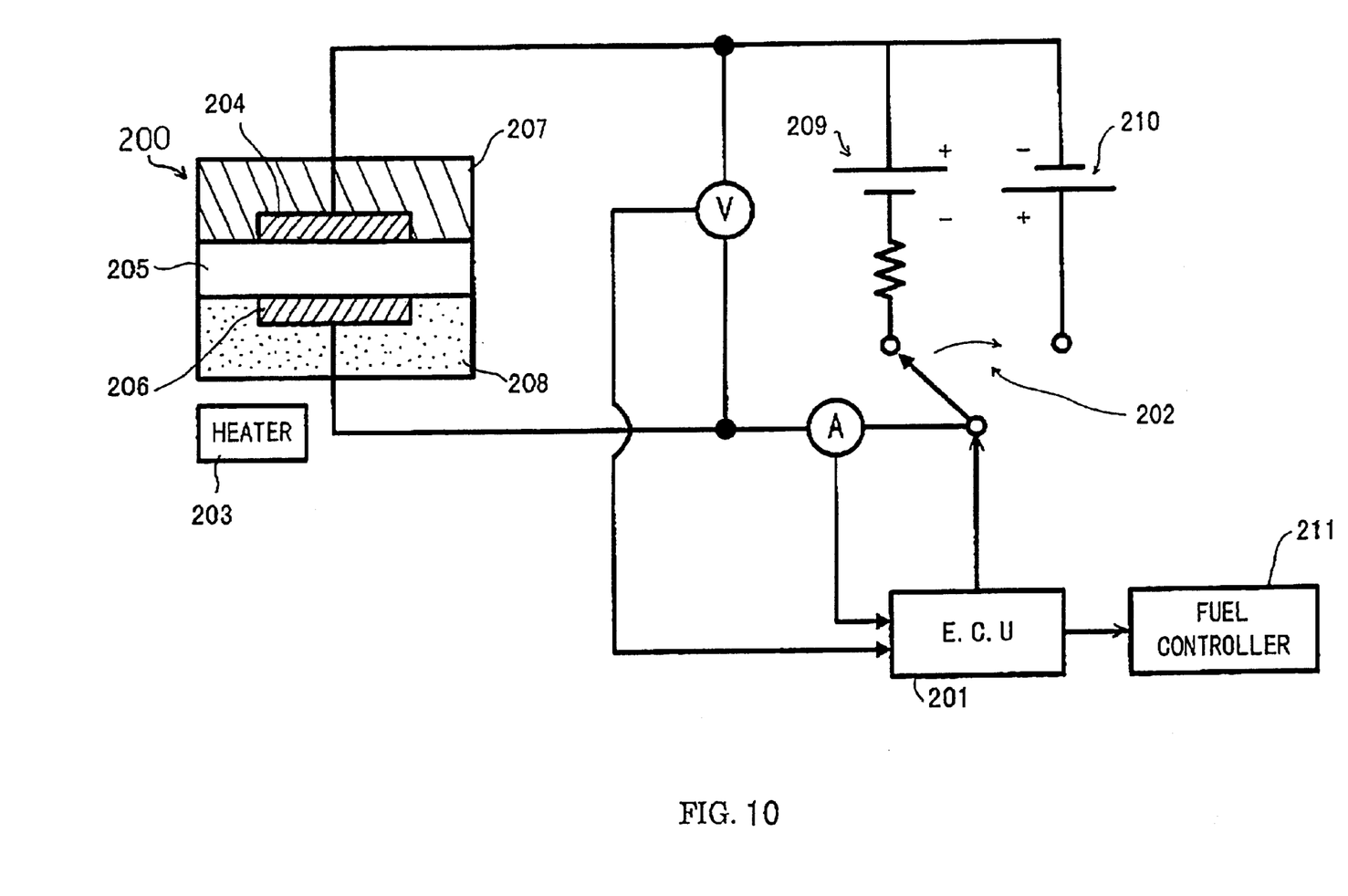
FIG. 10 is a schematic diagram described a concept on a method of detecting two types of air/fuel ratios by using an air/fuel sensor having a electrochemical cell according to the invention.

FIG. 10 shows a schematic diagram describing a concept on a method of detecting two types of air/fuel ratios by using an air/fuel sensor having a electrochemical cell according to the invention.

Referring to FIG. 10, a method of detecting two types of air/fuel ratios by using an air/fuel sensor with one electrochemical cell, according to the invention, is described hereinafter.

The air/fuel ratio sensor that is one of the embodiments according to the present invention is shown as the numerical number 200. The air/fuel ratio sensor 200 comprises an electrochemical cell comprised of an oxygen ion conductive solid electrolyte plate 205 and two electrode layers 204, 206 formed on the plate 205. The electrode layers 204, 206 are made of porous noble metal. One of the electrode layers 204, 206 is defined as an oxygen reference electrode 204 and the other one is defined as a measurement electrode 206.

The sensor 200 further comprises a high or rather strong diffusion limit cover 207 formed on the electrode 204. An oxygen reference chamber may be formed in at an interface between the strong diffusion limit cover 207 and the oxygen reference electrode, as is referred by the numerical number 55 in the air/fuel sensor in FIG. 5B. Such an oxygen reference chamber stabilizes an enough oxygen formation at the reference electrode 204 when the oxygen ions are pumped in or out through the electrolyte plate 205.

A weak or rather low diffusion limit cover 208 is formed on the measurement electrode 206. The strong diffusion limit cover 207 needs a gas diffusion resistance about 100 to 10,000 times higher than the weak diffusion limit cover 208, in order to accomplish the objects of the invention. The cover 207 may preferably have about 1000 to 4000 times higher gas diffusion limiting performance than the cover 208. Such a difference in the gas diffusion resistance between the two covers 207, 208 can be made by utilizing a porosity-lower ceramic cover and a porosity-higher ceramic cover 207 for the strong diffusion limit cover and the weak diffusion cover 208, respectively.

A heater 203 may be attached on the week diffusion limit cover 208 and positioned close to the cover 208 but away from the strong diffusion limit cover 207.

In order to make this one cell sensor 205 perform a dual sensing mechanism that has a $\lambda$ mode sensing (i.e. detecting a stoichiometric air/fuel ratio in the vicinity of $\lambda=1$) and a lean mode sensing (i.e. detecting a fuel-lean air/fuel ratio in the fuel-lean region of $\lambda>1$), a direct-current voltage is constantly applied across the electrodes 204, 206 while alternating or rather reversing a polarity of the direct-current voltage. Specifically, for example as shown in FIG. 10, when a dc voltage power supply 209 supplies a positive voltage to the oxygen reference electrode 20 7 and a negative voltage to the measurement electrode 206 to cause an constant electric field across the oxygen ion conductive solid electrolyte plate 205, the porous reference electrode 204 gathers oxygen ions through the electrolyte plate 205 from the measurement electrode 206 and forms a oxygen-concentration constant gas in pores of the reference electrode 204.

Under this voltage polarity condition, when a measurement gas contacts the sensor 200, the measurement electrode 206 can react with the measurement gas oxygen faster than the reference electrode 204 due to the gas diffusion difference between the two covers 207, 208. If the measurement exhaust gas is in a fuel-rich state (i.e. very low in oxygen content) at this moment, the cell does not produce the EMF causing any abrupt or sharp drop in the voltage that appears in a voltmeter V inserted between the electrodes 204, 206 as shown in FIG. 10.

If the gas in a fuel-lean state (i.e. including some oxygen amount) contacts the sensor 200, the EMF produced in the cell instantly causes the cell resistance to decrease sharply resulting in a abrupt drop of the voltage appearing in the voltmeter V between the electrodes 204, 206.

If the voltage value detected by the voltmeter is fed to the control unit (ECU) 201 that controls a fuel injector 211, as shown in FIG. 10, the ECU can control an air/fuel condition in the engine to be adjusted close to a stoichiometric air/fuel ratio (i.e. $\lambda=1$) . This means that this sensor can be used as the stoichiometric air/fuel ratio sensor i-e $\lambda$ oxygen sensor but not as an wide range air/fuel ratio sensor that can detect the oxygen concentration state of the gas i.e. the value of $\lambda$ is in $\lambda>1$.

Still referring to FIG. 10, in order to detect such a value $\lambda$ in $\lambda>1$ with the sensor 200, the voltage applied previously is reversed. For instance, the voltage polarity given by the dc power supply 209 is changed to a reverse polarity voltage supply 210 by a switch 202.

Under the reversed polarity, the oxygen in the pores of the reference electrode becomes zero. Therefore, when the fuel lean gas i.e. oxygen containing gas contacts the sensor 200, the measurement electrode 206 exposes to more oxygen molecules in the gas than the reference electrode 204. In this state, the EMF is produced in the cell by the oxygen concentration difference between the electrodes 204, 206, and a current flow appears in the current meter A inserted between the measurement electrode 208 and the reverse polarity voltage supply 210. This current is proportional to the oxygen concentration of the measurement gas. Therefore, the oxygen concentration of the gas is determined in a wide range as far as the gas is in the fuel-lean mode. If the current is very small below a predetermined level, then the polarity between the electrodes 204, 206 is switched to a previous $\lambda$ mode voltage applied state.

Thus as described above, by using the air/fuel ratio sensor comprised of one cell and the diffusion limit covers formed on the cell electrodes, both the stoichiometric air/fuel ratio and air/fuel ratios in a wide range of the fuel-lean region is detected.

What is claimed is:

1. A single-cell stoichiometric air/fuel ratio sensor for sensing oxygen in an exhaust gas, said sensor having a plurality of substantially planar laminated layers defining a plate detecting portion and a plurality of substantially planar laminated layers defining a plate heater portion adjacent to said detecting portion for heating said detecting portion comprising:

a solid plate electrolytic body having first and second opposed major surfaces and a perimeter edge;

a first porous electrode disposed on said first major surface and comprising an electrode reaction portion and a lead portion, said lead portion extending from said reaction portion to a location at said perimeter edge, said first porous electrode being operative as a measurement electrode;

a second porous electrode disposed over said second major surface and comprising an electrode reaction portion and a lead portion, said lead portion extending from said reaction portion to a location proximate said perimeter edge, said second porous electrode being operative as a reference electrode;

a first protective layer covering at least said reaction portion of said measurement electrode, said first protective layer being porous and the rate of oxygen diffusion through said first protective layer being substantially uncontrolled; and a controlled ventilation means formed adjacent to said electrolytic body and comprising a passage providing oxygen contact with at least a part of said second porous electrode, the rate of oxygen diffusion through said controlled ventilation means being substantially controlled to an amount less than the rate of diffusion through said first protective layer, wherein said heater portion is disposed closer to one of said first and second porous electrodes that the other of said electrodes.

2. An air/fuel ratio sensor according to claim 1, wherein said controlled ventilation means has a gas diffusion limiting resistance of about $10^2$ to $10^4$ times higher than that of the first protective layer.

3. An air/fuel ratio sensor according to claim 2, which further comprises a heater positioned closer to the first protective layer formed on the electrode than to the controlled ventilation means formed on the other electrode.

4. An air/fuel ratio sensor according to claim 1, which further comprises voltage supply for supplying a predetermined voltage to said electrodes and a voltage switch for switching a polarity of the voltage applied across the electrodes.

5. An air/fuel sensor according to claim 1 wherein the controlled ventilation means comprises a porous body forming a lead portion of said second electrode, said lead portion being, in use, exposed via a connecting hole to said exhaust gas, and said controlled ventilation means functions as a rate-determining ventilating portion for substantially controlling the rate of oxygen diffusion between said second electrode and the exhaust gas.

6. An air/fuel sensor according to claim 5 wherein said rate-determining ventilating portion is a porous body disposed in the connecting hole for connecting the lead portion of said second electrode and said exhaust gas.

7. An air/fuel ratio sensor according to claim 5, wherein said rate-determining ventilating portion is disposed on a side of said electrolytic body having a temperature lower than a temperature of the other electrode.

8. An air/fuel ratio sensor according to claim 1, wherein said plate detecting portion and said plate heater portion are laminated, then fired at the same time to form an integral structure.

9. An air/fuel ratio sensor according to claim 8, wherein said plate detecting portion and said plate heater portion are laminated via a porous body.

10. An air/fuel ratio sensor according to claim 1, wherein said plate detecting portion having said electrodes and said solid electrolytic body and said plate heater portion are disposed close to each other with a clearance therebetween.

11. The air/fuel sensor of claim 1 wherein said first protective layer is exposed at the perimeter to the exhaust gas.

12. The air/fuel sensor of claim 11 wherein said controlled ventilation means comprises a hole for oxygen-transport connecting said reference electrode to said exhaust, said hole extending from said reference electrode to a perimeter of said body.

13. The air/fuel sensor of claim 12 wherein a diffusion control material is disposed in said hole.

14. The air/fuel sensor of claim 1 wherein said controlled ventilation means comprises a hole for oxygen-transport connecting said first protective layer to said second porous electrode.

15. The air/fuel sensor of claim 14 wherein said second porous electrode lead portion comprises a material with a density higher than that of the reaction portion.

16. The air fuel sensor of claim 1 wherein said first protective layer is exposed on a major planar surface to the exhaust gas.

17. The air/fuel sensor of claim 16 wherein the controlled ventilation means comprises a clearance portion for oxygen transport connecting said first protective layer and said reference electrode.

18. The air/fuel sensor of claim 1 wherein said detection portion is adhesively bonded to said heater portion.

19. The air fuel sensor of claim 1 wherein said controlled ventilation means comprises a nonporous layer disposed in a plane adjacent to and covering at least a portion of said second porous electrode.

20. The air fuel sensor of claim 1 wherein a substantial part of the reaction portion of said second electrode is spaced apart from the second major surface of said electrolytic body.

21. The air fuel sensor of claim 1 wherein a substantial part of the reaction portion of said second electrode is in direct contact with said second major surface of said electrolytic body.

* * * * *